United States Patent [19]

Taylor et al.

[11] Patent Number: 5,192,507

[45] Date of Patent: * Mar. 9, 1993

[54] RECEPTOR-BASED BIOSENSORS

[75] Inventors: Richard F. Taylor, W. Boxford; Ingrid G. Marenchic, Walpole; Edward J. Cook, South Hamilton, all of Mass.

[73] Assignee: Arthur D. Little, Inc., Cambridge, Mass.

[*] Notice: The portion of the term of this patent subsequent to Mar. 19, 2008 has been disclaimed.

[21] Appl. No.: 664,440

[22] Filed: Mar. 4, 1991

Related U.S. Application Data

[63] Continuation of Ser. No. 203,281, Jun. 6, 1988, abandoned, which is a continuation-in-part of Ser. No. 58,389, Jun. 5, 1987, Pat. No. 5,001,148.

[51] Int. Cl.$^5$ .......................................... G01N 33/483
[52] U.S. Cl. .................... 422/68.1; 435/174; 435/181; 435/817
[58] Field of Search ............... 422/68.1; 435/174, 181, 435/817

[56] References Cited

U.S. PATENT DOCUMENTS

| | | |
|---|---|---|
| 3,833,894 | 9/1974 | Aviram et al. . |
| 4,004,979 | 1/1977 | Avarameas et al. ................... 195/68 |
| 4,078,049 | 3/1978 | Felix et al. .......................... 436/542 |
| 4,229,537 | 10/1980 | Hodgins et al. . |
| 4,298,685 | 11/1981 | Parikh et al. ........................ 436/527 |
| 4,307,195 | 12/1981 | Karasawa et al. . |
| 4,324,858 | 4/1982 | Goodson et al. ...................... 435/20 |
| 4,344,438 | 8/1982 | Schultz . |
| 4,352,884 | 10/1982 | Nakashima et al. . |
| 4,357,142 | 11/1982 | Schall et al. . |
| 4,367,072 | 1/1983 | Vogtle et al. . |
| 4,371,612 | 2/1983 | Matsumoto et al. . |
| 4,415,666 | 11/1983 | D'Orazio et al. .................... 435/179 |
| 4,418,148 | 11/1983 | Oberhardt ............................ 435/179 |
| 4,456,522 | 1/1984 | Blackburn . |
| 4,484,987 | 11/1984 | Gough .................................. 435/817 |
| 4,490,216 | 12/1984 | McConnell . |
| 4,518,527 | 5/1985 | Numa et al. . |
| 4,592,894 | 6/1986 | Panitz . |
| 4,637,861 | 1/1987 | Krull et al. . |
| 4,659,665 | 4/1987 | Freeman et al. ..................... 435/182 |
| 4,721,601 | 1/1988 | Wrighton et al. . |
| 4,839,017 | 6/1989 | Taniguchi et al. ................... 435/817 |
| 5,001,058 | 3/1991 | Konishi et al. ...................... 435/125 |

FOREIGN PATENT DOCUMENTS

| | | |
|---|---|---|
| WO84/03945 | 10/1984 | PCT Int'l Appl. . |
| WO87/03095 | 5/1987 | PCT Int'l Appl. . |
| 1318815 | 5/1973 | United Kingdom . |
| 2136130A | 9/1984 | United Kingdom . |

OTHER PUBLICATIONS

Vadgama, P., *J. Med. Engineer. and Technol.* 5:293-298, 1981.
Yager, P., U.S. Statutory Invention Registration H201 (Jan. 1987).
Canh, T. M., *Chem. Abstracts*, 88:132789 (1978).
Gotoh, M. et al., *Chem. Abstracts*, 107:191092 (1987).
International Search Report.

*Primary Examiner*—James C. Housel
*Assistant Examiner*—Lyle A. Alexander
*Attorney, Agent, or Firm*—Hamilton, Brook, Smith & Reynolds

[57] ABSTRACT

A method of immobilizing and stabilizing an active biological receptor in a polymeric film and receptor-based biosensors for determining an analyte of interest in a sample. The receptor-based biosensors include a polymeric film having a biological receptor capable of binding an analyte of interest immobilized therein according to the method of the present invention and an electrical means for determining the presence and quantity of the analyte. In particular, acetylcholine receptor and opiate receptor have been immobilized in a polymeric film made by combining the receptor, a material (e.g., bovine serum albumin, gelatin) capable of polymerizing and a polymerizing agent (e.g., glutaradehyde).

9 Claims, 5 Drawing Sheets

RECEPTOR-BASED BIOSENSORS

RELATED APPLICATIONS

This is a continuation of co-pending application Ser. No. 07/203,281 filed on Jun. 6, 1988 now abandoned, which is a continuation-in-part of U.S. Ser. No. 058,389, filed Jun. 5, 1987.

BACKGROUND

Biosensors are electronic devices which produce electronic signals as the result of biological interactions. Basically, a biosensor includes a biological receptor linked to an electronic transducer in such a way that biochemical activity is converted into electrical activity. The electronic component of the biosensor measures voltage (potentiometric), current (amperometric), light, sound, temperature, or mass (piezoelectric). Lowe, C. R., *Biosensors* 1:3–16(1985). The development of chemical microsensors has fostered the technology necessary for biosensors. For example, an interdigitated gold electrode with a semiconductor film coating has been utilized in measuring concentrations of organic and inorganic vapors. Wohltjen, J., *Analytical Chemistry* 56:87–103 (1984).

Two types of biosensors are known: enzyme-based or metabolic biosensors and binding or bioaffinity biosensors. Enzymatic or metabolic biosensors use enzymatic or metabolic processes to detect the product of the reaction which occurs between the incoming agent (substrate) and the immobilized receiver (e.g., an enzyme). Enzyme-based biosensors are best exemplified by enzyme electrodes, which are devices which utilize standard electrodes able to detect dissolved gases, such as oxygen or chemicals, such as urea, electronically. When enzymes attached to the electrodes catalyze a reaction, a gas or chemical is produced. This chemical or gas is detected by a specific electrode, for example, an oxygen or ammonia electrode. Perhaps the best known examples of enzyme electrodes are those which contain glucose oxidase or urease. They can be used to measure, respectively, glucose or urea, as well as to detect end products of multi-enzyme systems (for detection of other substrates). Such enzyme electrodes are well-defined and many are commercially available. Vadgana, P., *Journal of Medical Engineering Technoloqy*, 5:293–298 (1981); Solsky, R.6., *CRC Critical Review of Analytical Chemistry*, 14:1–52 (1983).

Bioaffinity sensors rely on biological binding events for detection of substances of interest. Taylor, R. F., *The World Biotech Report* 1986, *Vol.* 2, pp.7–18 (1986). The binding of the environmental substance (ligand) to the immobilized receptor produces a detectable change in the shape or conformation of the receptor and this produces an output signal. Detection of this change can utilize one of a number of methodologies, including optical (interference, refractive index, fluorescence, etc.), mechanical (mass or density) or temperature changes.

Until the present time, only antibodies or antigens have been used successfully for bioaffinity sensors. For example, Wasserman antibody in blood has been detected through the use of a membrane containing immobilized antigen. Aizawa, M., *et al., Journal of Membrane Science* 2:125–132 (1977). Upon interaction of antibody with antigen, a millivolt (mV) change in potential occurs across the membrane; the change is proportional to concentration of antibody present in the blood sample. Antibody-antigen binding is also used in a variety of optically-based biosensors. Place, J. F., *et al., Biosensors* 1:321–353 (1985). The basic action mechanism in this type of biosensor has not been defined, but appears to be a change in conformation of the immobilized receptor and/or a physical change in the immobilization media (e.g., weight, thickness, light absorbancy, etc.). These changes are detected and amplified electronically using appropriate transducer technology.

There have been attempts to develop other types of binding or bioaffinity sensors. For example, Yager describes a biosensor consisting of a polymerizable lipid bilayer which contains an active membrane protein (e.g., the acetylcholine receptor) and which separates two electrolyte-filled compartments. Synthetic phospholipids in the bilayer membranes are used as stabilizers, and the membrane proteins are incorporated through use of a modification of known methods. Changes in current across the receptor-containing membrane are described as occuring when cholinergic agents are bound and measured using a known (electrode patch) technique. Yager P., U.S. Statutory Invention Registration H201 (Published Jan. 6, 1987).

Others have described efforts to immobilize enzymes and other "bioactive" materials onto glass (U.S. Pat. No. 4,357,142) and other surfaces, such as those containing acrylate copolymer (U.S. Pat. No. 4,352,884) or an acrylonitrile polymer (U.S. Pat. No. 4,371,612). See also U.S. Pat. No. 4,307,195; U.S. Pat. No. 4,456,522; U.S. Pat. No. 4,415,666; U.S. Pat. No. 4,418,148; and U.S. Pat. No. 4,484,987.

Although antibody- or antigen- based biosensors are useful in detecting ligands in samples, they have limitations, such as over-selectivity and near irreversible binding, which make it impossible to use them in many instances. Biosensors which are binding sensors or bioaffinity sensors, and which make use of a receptor other than an antibody or an antigen would be very valuable and find use in many contexts in which presently-available binding sensors cannot be used.

DISCLOSURE OF THE INVENTION

The present invention relates to receptor-based or bioaffinity sensors and to a method of immobilizing and stabilizing receptors in such sensors. The sensors of the present invention can be used to determine an analyte (or a specific class of analytes) of interest in a liquid or high-water gel. Sensors of the present invention make use of a substance, referred to as a biological receptor, which binds directly to the analyte of interest. This direct binding provides a means of directly detecting and measuring the binding event (between receptor and analyte or class of analyte). The receptor-based biosensor of the present invention can, as a result, be used to detect and to quantitate the analyte of interest. A preferred embodiment utilizes an interdigitated electrode, (contacting the receptor) to measure the impedance of the bound analyte. This measurement yields the concentration of the analyte of interest in the sample being measured. These receptor-based sensors have an important advantage over presently available enzyme-based biosensors, whose function relies on diffusion of a reaction product (i e., a product of a reaction involving an analyte to be measured) to an electrode at which it is detected.

In one embodiment of the present invention, the biological receptor is the acetylcholine receptor, which is immobilized and stabilized according to the method of the present invention, and used to determine the presence and quantity of acetylcholine or related cholinergic analytes in a sample. In another embodiment of this invention, the receptor is the opiate receptor which is similarly immobilized and stabilized and used to determine in a sample the presence of opiates, narcotics and other drugs which bind to or in some manner affect (interact with) the opiate receptor. In other embodiments of the present invention, the biological receptor can be an antibody, antigen or receptor for hormones, other neural transmitters, vitamins, bacteria, viruses, antibodies and serum lipoproteins. An antibody is a specific receptor for one substance; the other receptors, however, are capable of reacting with more than one substance (i.e., the substance to which they naturally or normally bind and other substances which have similar chemical or physical structures).

Receptor-based biosensors of the present invention provide a means of determining (e.g., detecting and/or quantifying) the presence in a sample of a wide variety of natural and synthetic substances. They are useful in health care, veterinary, agricultural, petrochemical, and pollution monitoring contexts, and are able to provide real-time information about levels of substances of interest or concern. Because of their simplicity and ability to directly measure a binding event which occurs between an appropriately-selected immobilized receptor and ligand (analyte of interest), they present a significant advancement over current detection, monitoring and process control devices.

DETAILED DESCRIPTION OF THE INVENTION

Figure 1:
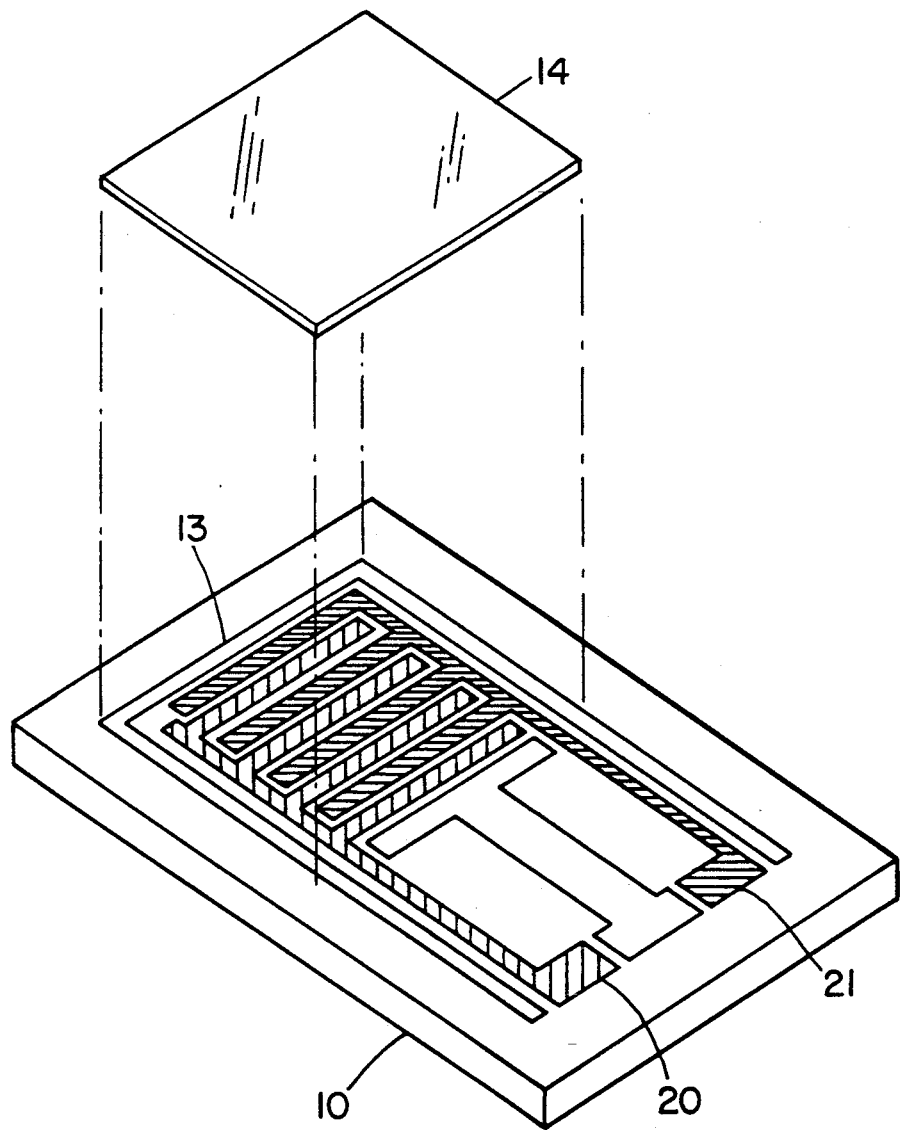
FIG. 1 represents a receptor-based biosensor of the present invention in which a single-chip design is used.

The present invention relates to receptor-based or bioaffinity sensors for the determination of an analyte (or a specific class of analytes) of interest in a sample, and to a method of immobilizing and stabilizing a receptor in the bioaffinity sensor. The receptor-based sensor of the present invention includes a polymeric film in which a receptor selected for its capability to bind an analyte of interest is incorporated.

The receptor-based sensor can be used to determine an analyte of interest in a sample which is a liquid or high-water gel. In addition, it can be used for the determination of an analyte of interest in a gas (e.g., air). In this application, known techniques for transfer of a gaseous air sample to a liquid stream are used to provide the liquid to be presented to the sensor.

In the sensor of the present invention, an appropriately-selected receptor is immobilized by copolymerization with a base component, such as gelatin, bovine serum albumin, human serum albumin, acrylic acid, methacrylic acid, collagen or other materials which polymerize. Polymerization can be effected using any means by which it is possible to polymerize the base component and the biological receptor and retain the capability of the biological receptor to bind an analyte of interest. For example, polymerization is effected chemically, such as by addition of a polymerizing catalyst or initiator or a crosslinking agent, such as glutaric dialdehyde (glutaraldehyde), to the receptor and base component combination. Other materials which can be used for this purpose include SPDP, dimethyl suberimidate, disuccinimidyl suberate and bismal bimidonexane. The receptor is selected on the basis of its ability to bind to an analyte of interest to be determined in a sample. As used herein, the term analyte of interest refers to an individual analyte of interest or a specific class (or type) of analyte bound by a receptor.

In one embodiment, a receptor which is an active cell membrane protein is immobilized by being combined with bovine serum albumin and a polymerizing agent or crosslinking agent such as glutaraldehyde. The resulting solution is mixed and cast onto transducers, where it polymerizes as a membrane coat in which the cell membrane protein is incorporated.

In a specific embodiment in which the receptor is an active cell membrane protein, the neural transmitter acetylcholine receptor is combined with bovine serum albumin (e.g., 99% globulin-free, Sigma Chemical Co.). Glutamic dialdehyde is added to the reaction mixture to effect polymerization. The solution is mixed and cast onto transducers, generally within 5 to 20 minutes after glutaraldehyde addition. This results in formation of a membrane coat (through polymerization) on the transducers. It is allowed to age on the transducers prior to use; aging generally continues for 16-24 hours prior to use. In a further embodiment, one or more materials are added to the solution to stabilize acetylcholine receptor activity in the membrane. These additives include, but are not limited to, phosphatidylcholine, alpha-tocopherol, butylatedhydroxyanisole (BHA), cholesteryl palmitate, Triton TM X-100, sodium cholate, cetyltrimethylammonium bromide (CTAB), Tween-80 TM and Zwittergents TM 3-10 and 3-08. Addition of combinations of these additives, such as a combination of phosphatidyl choline with Triton TM X-100, sodium cholate or Zwittergents TM, results in a marked increase in stability of the acetylcholine receptor, at the time of immobilization and after prolonged storage. For example, incorporation of phosphatidyl choline and Triton TM X-100 into the film increased retention of binding activity of AChR after 50 days at 4° C. by more than 90% (compared to the immobilized AChR with no phosphatidyl choline and Triton TM X-100). That is, after 50 days at 4° C., the AChR without stabilizer had lost 90% of its binding activity, compared with the AChR with stabilizer.

In another embodiment in which the receptor is a cell membrane-integrated receptor, the neuronal-cell membrane opiate receptor (OpR) is combined with bovine serum albumin and polymerization is initiated with glutaraldehyde. The mixture is cast on transducer chips. Preparation of the opiate receptor as used in the sensor of the present invention, its immobilization and application to transducer chips are described in detail in Example 2. Briefly, bovine serum albumin (BSA), a stabilizer and CHAPS (see Example 2) were solublized in an OpR preparation. Glutaraldehyde was added to effect polymerization. The resulting membranes were cast onto glass plates (for stability studies) or onto interdigitated electrode transducers. Alternatively, the OpR was immobilized in gelatin membranes by solubilizing gelatin in an OpR preparation and adding glutaraldehyde to effect polymerization.

Challenge by opiates of OpR-containing transducers in which OpR was immobilized in BSA demonstrated the ability of such transducers to respond to opiates (i.e., naloxone, levorphanol).

In another instance, the immobilized receptor is an antibody or an antigen and is immobilized in much the same manner as previously described for the cell membrane protein. For example, an antibody such as immunoglobulin G (IgG) is immobilized in the following way: antibody, bovine serum albumin, and a polymerizing agent, such as glutaraldehyde, are combined. The resulting solution is mixed and cast onto transducers, where it polymerizes as a membrane coat. In a specific embodiment, IgG and bovine serum albumin are combined and glutaraldehyde is added to effect polymerization. The solution is mixed and cast onto transducers, on which it polymerizes as a membrane coat, in which the antibody (or antigen) is incorporated. After the membrane coat is aged for sufficient time (e.g., for 16-24 hours) prior to use.

There are many additional types of biological receptors, useful in the receptor-based sensor of the present invention, which can be immobilized and stabilized according to the method of the present invention.

Other biological receptors include those for hormones, neural transmitters other than the acetylcholine receptor (e.g., adrenergic, gamma aminobutyric, serotonergic, dopaminergic), vitamins and other nutrients, bacteria, viruses, serum lipoproteins and antibiotics. These other receptors, unlike a single antibody, can react with more than one substance. Thus, in addition to binding their "natural" ligands (i.e., those to which they are intended to bind or bind in living organisms), these other receptors can bind substances whose chemical or physical structure is similar to the chemical or physical structure of the natural ligands. Such "class" binding is the basis for drug activity and the toxicity of many substances. For example, the acetylcholine receptor (AChR) described above is normally present in animals and acts as a mediator of neural transmission. The acetylcholine receptor is bound in the membrane of nervous tissue cells and, upon interaction with acetylcholine (its natural ligand), changes conformation and initiates a series of membrane ionic charge changes, which, in turn, result in a nerve impulse.

At least two types of other substances can also bind to the acetylcholine receptor: substances which cause changes in the AChR and, ultimately, nerve stimulation and substances which block changes in the AChR conformation and, thus, block nerve stimulation. For example, substances such as muscarine, phencyclidines, etc., can cause these conformational changes in the AChR and cause nerve stimulation. Substances such as nicotine, curare and the snake toxin alpha-bungarotoxin, can also bind to the AChR. These substances, however, block the ability of the AChR to change conformation and block nerve stimulation. As a result, an acetylcholine receptor-based biosensor of the present invention is useful to detect and quantify compounds or substances which act on the receptor. For example, such a biosensor is useful for the determination of organophosphorus compounds (e.g., diisopropylfluorophosphate, soman, sarin, VX) drugs (e.g., succinylcholine, nicotine, decamethonium, pilocarpine, carbachol, physostigmine), naturally-occurring toxins (including alpha bungarotoxin curare; atropine; homarine) and a variety of environmental chemicals and pollutants (e.g., malathion, diazinon, carbaryl). As a result, a sensor of this type can be used to determine such substances in, for example, situations in which chemicals or pesticides are made (e.g. manufacturing plants) or used (e.g., agricultural or farming uses, home gardening uses, defense applications), as well as in situations in which their presence and/or concentrations are monitored (e.g., water supplies, air concentrations). It also has medical applications (e.g., in a clinic, hospital, physicians practice) in determining drugs, viruses, hormones, toxins, etc. in patients.

Another example of a membrane-associated receptor which is able to react with more than one substance, which is useful in the sensor of the present invention, is the opiate receptor (OpR).

The opiate receptor is a naturally-occurring biological macromolecule which is located in a variety of animal tissues, including the brain, spinal cord, hypothalamus and intestine. The receptor is a membraneintegrated receptor, i.e., it is physically part of neuronal cell membranes. It appears to be an aggregate of protein components with associated lipid and carbohydrate components and to have a molecular weight of from 300,000 to 400,000. The receptor binds specific drugs, narcotics and hormones, such as demorel, darvon, morphine, heroin, enkephalins and endorphins. The term opiate was at one time used to designate drugs derived from opium, such as morphine, codeine and semisynthetic congeners of morphine. The word opioid, however, is also used to refer to drugs, whether natural or synthetic, which are morphine-like or opium-like in their actions, to varying extents. Opioids interact with what seem to be closely related receptors and share some of the properties of peptides such as eukephalins and the endorphins. The opiate receptor has been shown to have several subtypes or subspecies, such as mu, delta, kappa and sigma subtypes. Goodman and Gilman's *The Pharmacological Basis of Therapeutics*, A. G. Gilman et al. (ed.), Chapter 22, Macmillan Publishing Co., Inc. (1980). Drugs which binds OpR may do so by binding to a specific binding site, to secondary sites on the OpR, or to both.

Binding of the OpR to such a substance leads to activation (or blocking of activation) of an internal cellular enzyme which, in turn, leads to synthesis (activation) of a cyclic nucleotide within the cell. The cyclic nucleotide then causes a series of biochemical events which lead to the whole animal physiological response to the substance binding to the opiate receptor. The physiological responses include analgesic, antianxiety, euphoric, antidepressive, antitussive and antidiarrheal responses. Continued stimulation of opiate receptors with an opiate can lead to dependence and addiction to that opiate.

As a result of the ability of OpR to bind substances such as those described, an OpR-based biosensor of the present invention is useful in their detection and quantification in a sample. Such a biosensor will be especially useful in medical settings (hospitals, physicians' offices, clinics) in which determination of the presence or absence of a drug or other substance which binds OpR is desired for screening samples (e.g., blood, urine) or in which quantification of the substance is to be carried out.

The following description illustrates the components and function of biosensors in which the receptors are the opiate and acetylcholine receptors. However, the same description is applicable to a biosensor of the present invention in which different biological receptor is incorporated; the following description is not meant to be limiting in any way.

AChR-Based Biosensor

As described previously, acetylcholine receptor (e.g., $N_2$ nicotinic acetylcholine receptor from *Electrophorus electricus* (eel), partially purified) is combined with a film base (e.g., bovine serum albumin), a polymerization catalyst (e.g., glutaraldehyde) and at least one stabilizer (e.g., phosphatidylcholine or Triton TM X-100). The resulting solution is cast onto transducers, on which it polymerizes, forming a receptor-containing membrane.

In one embodiment of the present invention, which is represented in FIG. 1, a single-chip design is used, in which the transducer is a quartz or glass substrate 10 containing two-terminal interdigitated gold electrodes 20 and 21. A receptor-containing membrane 14 is contacting the interdigitated area of the gold electrodes and, in this instance, is an acetylcholine receptor membrane. An alternating current field across the electrodes is used to detect binding of substances (analyte of interest) to the immobilized receptors. For example, when the biosensor contains immobilized acetylcholine receptor and a ligand (analyte of interest), such as acetylcholine or alpha-bungarotoxin, is present in a sample being analyzed, binding of the receptor and the analyte of interest occurs, producing changes in the alternating current impedance of the biosensor. The changes are directly proportional to the concentration of the ligand of interest to which the biosensor is exposed (e.g., by contact with a sample). Similary, when human immunoglobulin G is the receptor included in the biosensor and antibody to it is present in a sample being tested, changes in the alternating current impedance of the biosensor occur and are directly proportional to the concentration of ligand (i.e., antibody to immunoglobulin G) present. In both cases, a fixed frequency of, for example, 120 Hz or 1 kHz and a fast-responding digital LCR meter are used. A single chip test circuit is represented schematically in FIG. 2.

In one embodiment of the biosensor of the present invention, a double chip design is used. This double biosensor includes a non-receptor (control) membrane and a receptor-containing membrane. The control membrane serves as a detector for background, nonspecific binding to the membranes. Any signal from such binding to the control membrane is subtracted from the signal resulting from the receptor-containing membrane. As a result only signal related to specific ligand-receptor binding is reported.

Figure 3A:
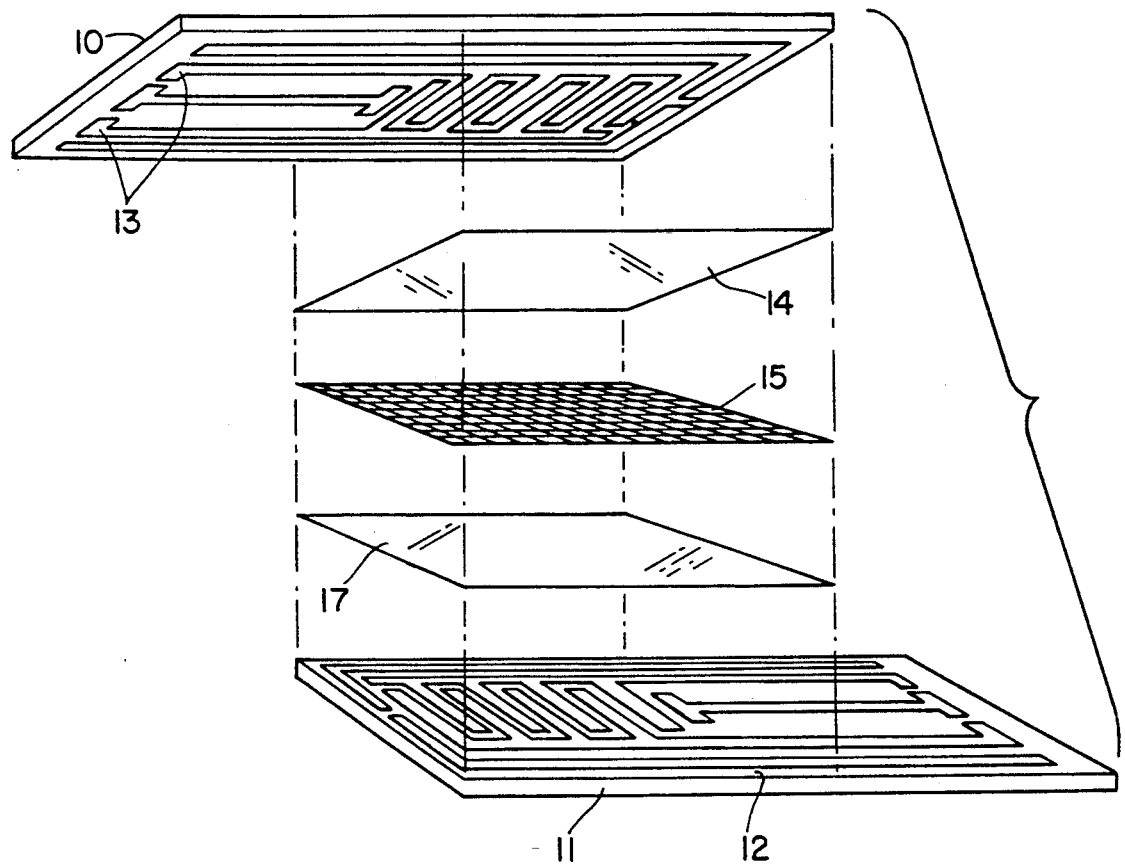
FIGS. 3A and 3B represent a receptor-based biosensor of the present invention in which a differential (double) chip design is used.
Figure 3B:
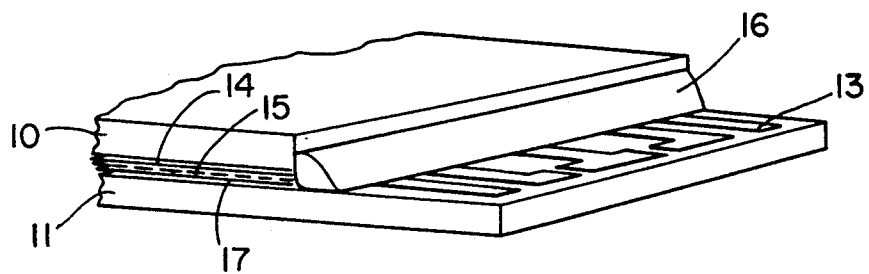

FIGS. 3A and 3B illustrate the double biosensor apparatus with its various components. A conductor 13 is evaporated through a mask to form an interdigitated pattern on each substrate 10 and 11. In a preferred embodiment, gold is evaporated onto each silicon dioxide substrate, 10 and 11, forming a 1-2 micron layer. A bonding agent 12 (typically Mg, Ti, or Zr) is used to insure good adhesion of the gold to the $SiO_2$ substrate. The biological receptor 14 chosen for a particular embodiment is then formed on the interdigitated section of one conductor. The receptor surface 14 of the substrate 10, for example, is then positioned face to face with a reference membrane 17 associated with substrate 11. An equipotential barrier 15 is interposed between the receptor surface 14 and membrane 17. The barrier 15 serves to inhibit current flow between the two receptor surfaces and may be comprised of an insulator or a suitably biased conductor. Seal 16 defines and seals a volume between the membrane surfaces. This volume is filled with material to be analyzed, or alternatively, placed in a fluid stream that is being analyzed. The present invention allows the sampling of very small volumes of a process stream while retaining high sensitivity to variations in the spacial or temporal changes in the concentration of the material being analyzed. Traditional microfabrication techniques may be used in making these microsensors.

Figure 4:
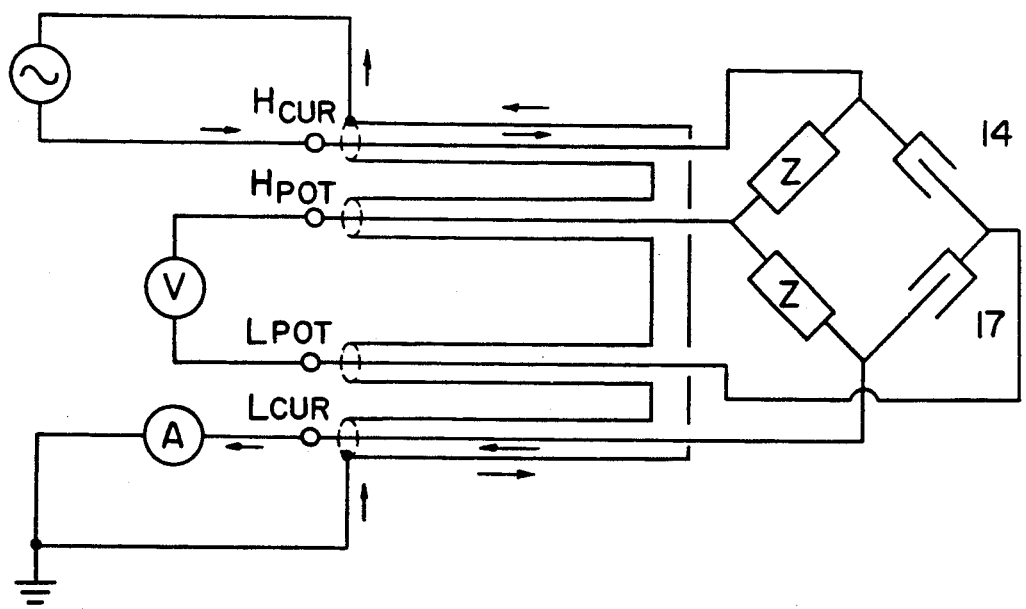
FIG. 4 is a graphic representation of a differential (double) chip test circuit.

FIG. 4 shows a standard bridge circuit for measuring the impedence across the receptor membrane 14. The impedance of the reference membrane must be large with respect to the receptor membrane, but small with respect to the impedance of the instrumentation. This differential measurement yields ½ of the difference in the impedance betweeen the reference membrane and the receptor membrane.

Such a biosensor would be useful to detect and measure ligand concentrations in clinical settings (e.g., blood and urine samples), in environmental and industrial settings (air and water) and in industrial process streams (e.g., fermentation broths and chemical syntheses solutions).

OpR-Based Biosensor

An opiate receptor-based biosensor of the present invention can be produced in a manner similar to that used in producing the AchR-based biosensor. Preparation of the OpR, its immobilization and production of interdigitated transducer chips bearing OpR-containing membranes are described in detail in Example 2.

Briefly, OpR from rat brain is used to produce such a biosensor by combining it with a film base (e.g., bovine serum albumin), a polymerization catalyst (e.g., glutaraldehyde), at least one stabilizer (e.g., phosphatidyl choline) and CHAPS solution (see Example 2). In one embodiment, approximately 2-10 mg OpR protein is present in the membrane formed when the resulting combination is cast onto transducers, on which it polymerizes (forming an OpR-containing membrane).

The same embodiments (e.g., a single-chip design and a double biosensor apparatus) described previously, with reference to FIGS. 1–4, for the AChR-based biosensor of the present invention can also be used for the OpR-based biosensor.

Other Receptor-Based Biosensors

Receptors can bind a range or class of substances which have similar structures and physiological activity. Because receptors can also distinguish whether a substance will stimulate or block the receptor-mediated physiological response, they represent sophisticated detectors for chemicals such as therapeutic and abused drugs, insecticides, toxic agents, hormones, etc. Examples of known receptors include neural receptors, such as cholinergic, adrenergic, gamma aminobutyric, serotonergic, and dopaminergic receptors; hormonal receptors such as opiate, steroid, and insulin receptors; nutrient receptors, such as cholesterol and vitamin receptors; and cell surface receptors, such as lectin, viral, antibiotic and low density lipoprotein (LDL) receptors. Additionally, plants contain specific receptors for growth hormones (and related toxins), such as auxin, cytokinins and indoleacetic acid. Such receptors can also be used, with modification as needed, of the methods described above (for AChR- and OpR-based biosensors, in making biosensors of the present invention.

The subject invention will now be illustrated by the following examples, which are not to be seen as limiting in any way.

EXAMPLE 1

Acetylcholine Receptor-Based Biosensor Receptor Preparation

Acetycholine receptors to be used in the biosensor of the present invention were prepared according to the method below, which is a modification of methods described by Klett et al. and Karlin et al.. Klett, R. P. et al., Journal of Biological and Chemistry, 248:6841–6853, (1973); Karlin, A. et al., Methods in Receptor Research (Belcher, M., ed), p. 1–35 (1976).

Approximately 50 g of minced electric organ tissue from the electric eel (Electrophorus electricus) was homogenized in 150 ml of lmM EDTA pH 7.4, for 1 min. The homogenate was filtered through cheesecloth to remove solid matter, and the filtrate was centrifuged at 20,000 × g for 15 min at 4° C. The resulting pellet was homogenized for 30 sec in 100 ml of 50 mM $Na_2HPO_4$—$KH_2PO_4$ buffer, pH 7.4, containing 0.02% sodium azide and centrifuged again at 20,000 × g for 15 min at 4° C. The resulting pellet was homogenized for 30 sec in 20 ml of 10 mM $Na_2HPO_4$—$NaH_2PO_4$ buffer, pH 8, containing 50 mM NaCl, (mM EDTA and 3% Triton TM X-100). The homogenate was gently stirred at room temperature for 60 min and then centrifuged at 100,000 × g for 60 min at 4° C. The resulting supernatant was adjusted to pH 7.4 with 0.6M $Na_2HPO_4$, and approximately 10 ml was applied to a 1.5×40 cm 40 cm column of Sephadex TM G-50 (Pharmacia, Piscataway, N.J.). The column was equilibrated and eluted with 0.02M $Na_2HPO_4$-$KH_2PO_4$ buffer, pH 6.8, containing 2% Triton TM X-100. The acetylcholine receptor elutes from the column in approximately 3 to 10 ml (void volume). This is hereafter referred to as the acetylcholine receptor (AChR).

The activity of the AChR was determined using the standard DEAE-filter disc binding assay. This method utilizes the binding of [$^{125}$I] alpha-bungarotoxin to determine AChR content in preparations. Schmidt, J. and M. J. Raftery, Analytical Biochemistry, 52:249–354 (1973).

Immobilization Formulations

The membrane formulation (basic membrane formulation) used for immobilization of both receptor and antibody included 300 mg of Bovine Serum Albumin (BSA, 99% globulin-free, Sigma Chemical Co., St. Louis, Mo.) in 0.02M $K_2HPO_4$ buffer (pH 6.8) containing 0.1% Triton TM X-100. In the case of the AChR-based sensor, the BSA was 4 ml of the buffer and 1 ml of AChR preparation was included in the basic membrane formulation. A coating solution which included approximately 2% (by weight) receptor preparation or approximately 0.5% AChR (by weight). On a per sensor basis, this represents approximately 10 ug (micrograms) of receptor preparation (see Example 1) or approximately 1-2 ug AChR. Sensors containing a wide range of levels of AChR (e.g. 0.1 ug to more than 100 ug) can be used. From 0.1 to 5% (by volume) of glutaric dialdehyde (glutaraldehyde) was added to the reaction mixture to effect polymerization. The solution was mixed and cast onto transducers within 5 to 20 min after glutaraldehyde addition. The solution polymerized as a membrane coat on the transducer within 15 to 45 min. It was allowed to age on the transducer for 16–24 hr prior to use.

In the case of antibody-containing membranes, up to 75 mg of antibody or antigen is added to 300 mg of BSA in 5 ml of the buffer described above. This is equivalent to coatings containing approximately 25% (by weight) IgG on a per sensor basis, which is approximately 250 to 500 ug of IgG per chip. Sensors containing a wide range of levels of IgG (e.g., 1 ug to 1000 ug) can be used. Glutaraldehyde is added for polymerization, and the resulting solution treated as described for the AChR-based sensor.

Selected materials were added to the basic membrane formulation to assess their ability to stabilize AChR activity in the membrane. These included phosphatidylcholine, alpha-tocopherol, butylatedhydroxyanisole (BHA), cholesteryl palmitate, Triton TM X-100, sodium cholate, cetyltrimethylammonium bromide (CTAB) Tween-80 TM, and Zwittergents 3-10 and 3-08. Varying concentrations of 0.1 to 5% by weight of combinations of these stabilizing agents were shown to markedly stabilize AChR activity immediately upon immobilization and after prolonged storage.

Table 1 summarizes the concentrations of each stabilizer tested in the membrane formulations. Individually, each stabilizer, when added to the basic membrane formulation into which AChR had been incorporated increased AChR stability (in comparison to non-stabilized membranes).

TABLE 1

| Stabilizers Added to Receptor Membranes | |
|---|---|
| Stabilizer | Amount |
| Sodium cholate | |
| CTAB | |
| Zwittergent TM 3-10 | |
| Zwittergent TM 3-08 | 0.1 to 5% by volume |
| Triton TM X-100 | |
| Tween TM 80 | |
| Phosphatidylcholine | 0.1 to 10% by weight |
| alpha-Tocopherol | 0.1 to 5% by weight |
| BHA | 0.001 to 1% by weight |
| Cholesteryl esters (e.g., palmitate) | 0.1 to 10% by weight |

Such stabilization was measured as retention of binding activity after immobilization after storage for at least 2 days at room temperature. Table 2 shows results of one set of experiments in which varying concentrations of detergents as stabilizers were used. As is shown by these data, Triton TM X-100 and sodium cholate were found to be the best stabilizing detergents.

TABLE 2

| Effect of Detergent Stabilizers on AChR Membrane Activity[a] | | |
|---|---|---|
| Detergent | % By Volume | % Activity Increase[b] |
| Triton TM X-100 | 0.1 | 12 |
| | 0.5 | 55 |
| | 1.0 | 85 |
| | 2.0 | 110 |
| Sodium cholate | 0.5 | 18 |
| | 1.0 | 110 |
| | 2.0 | 145 |
| Zwittergent TM 3-08 | 0.5 | 0 |
| | 1.0 | 55 |

TABLE 2-continued

Effect of Detergent Stabilizers on
AChR Membrane Activity[a]

| Detergent | % By Volume | % Activity Increase[b] |
|---|---|---|
|  | 2.0 | 55 |
| Zwittergent TM 3-08 | 0.5 | 20 |
|  | 1.0 | 30 |
|  | 2.0 | 38 |
| CTAB | 0.5 | 4 |
|  | 1.0 | 18 |
|  | 2.0 | 28 |

[a]24 to 48 hours after immobilization
[b]Over non-detergent containing membrane. Typically, such control membranes retain 20-30% AChR activity after immobilization.

Combinations of stabilizing agents were also tried. Results of these studies are shown in Table 3. The best of the combinations tested included detergent plus phosphatidylcholine.

TABLE 3

Effect of Detergents Plus Phosphatidyl Choline and BHA on AChR Membrane Activity[a]

| Detergent | % By Volume | Other Agent | % By Volume | % Activity Increase |
|---|---|---|---|---|
| Triton TM X-100 | 0.5 | PC | 0.6 | −50 |
|  | 2.0 | PC | 0.6 | 145 |
| Sodium Cholate | 0.5 | PC | 0.6 | 85 |
|  | 2.0 | PC | 0.6 | 285 |
| Zwittergent TM 3-10 | 2.0 | PC | 0.6 | 126 |
|  | 2.0 | PC | 1.5 | 129 |
|  | 2.0 | PC | 3.0 | 122 |
|  | 2.0 | BHA | 0.003 | 87 |
|  | 2.0 | BHA | 0.006 | 13 |
|  | 2.0 | BHA | 0.03 | 13 |

[a,b]See Footnotes Table 2.

Figure 5:
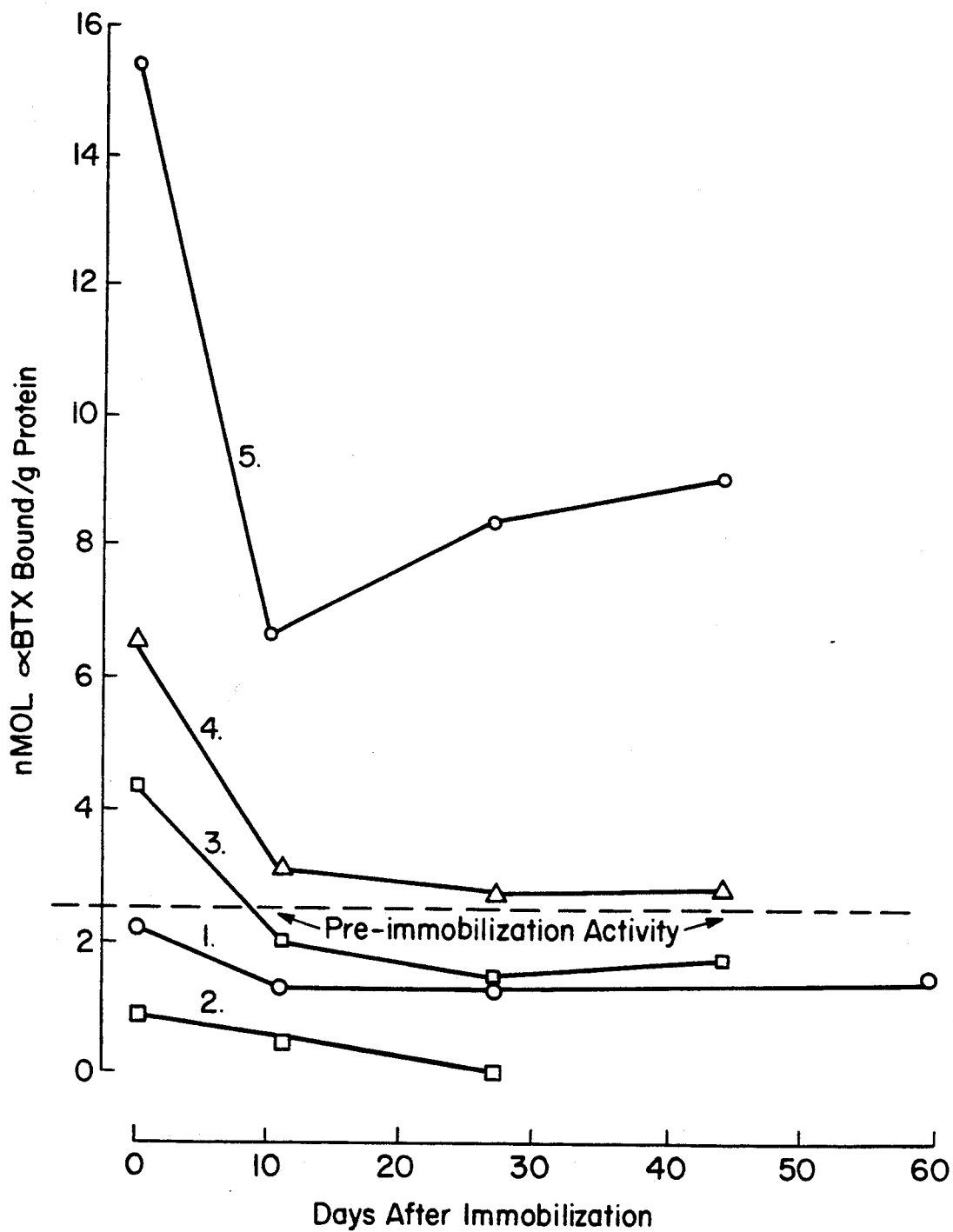
FIG. 5 is a graphic representation of retention of acetylcholine receptor binding activity at 4° C., after immobilization in five formulations.
Figure 6:
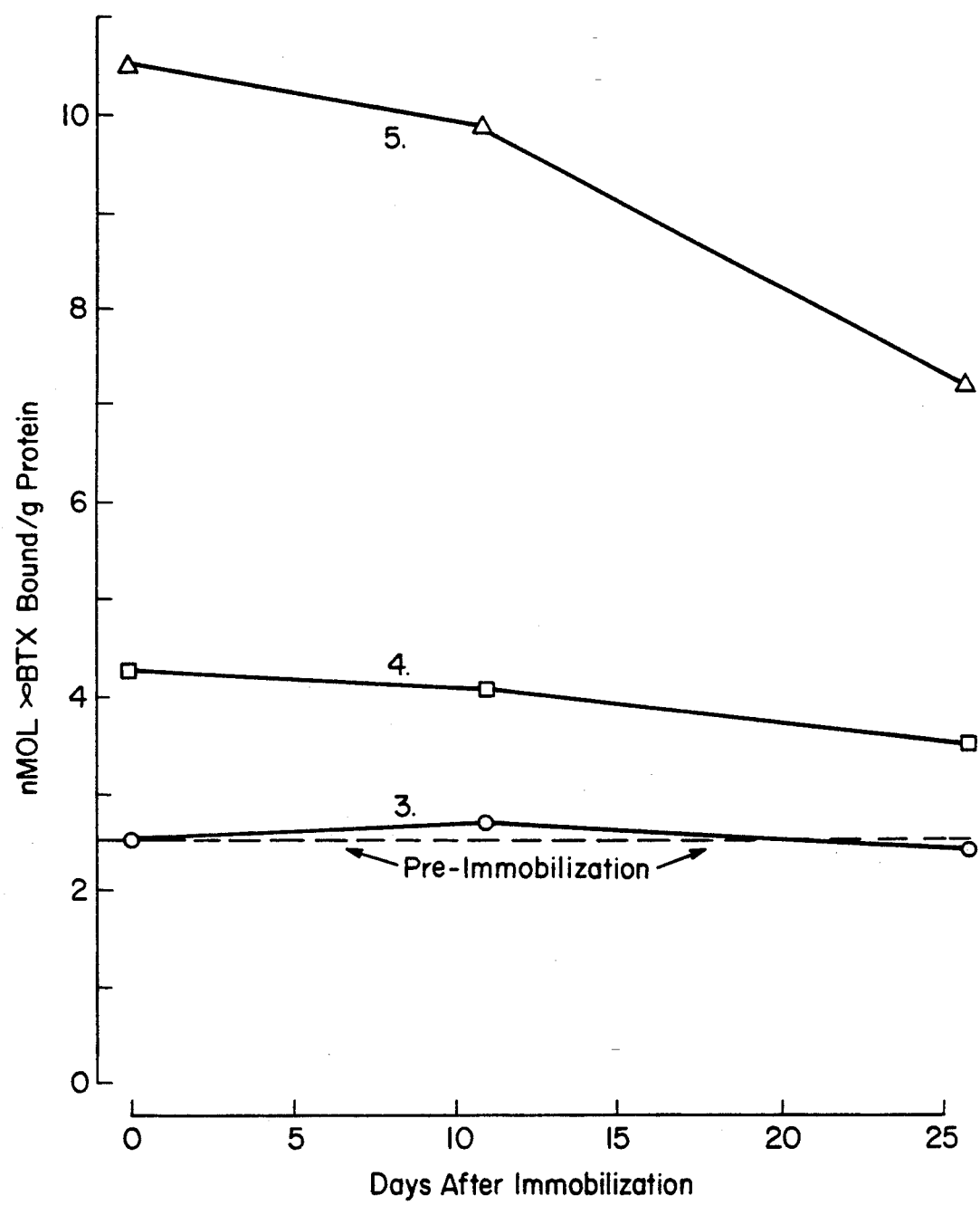
FIG. 6 is a graphic representation of retention of acetylcholine receptor binding activity at room temperature after immobilization in three formulations.

FIG. 5 is a graphic representation of activity retention (measured as binding of alpha-bungarotoxin) over time for a number of formulations. At 4° C., the most stable membranes were those containing Zwittergent 3-10 or sodium cholate, in combination with phosphatidylcholine. At room temperature, the most stable membranes over time were those containing Zwittergent TM 3-10 and phosphatidylcholine, sodium cholate and phosphatidylcholine or TX-100 and phosphatidylcholine, as shown in FIG. 6.

Detergent was shown not to affect antigen binding activity. This demonstrated that antibody-containing membranes can be prepared with or without addition of stabilizers.

A screening method was used to cast the receptor or antibody-containing membrane mixture over the electrode surface to a reproducible thickness which varied, for example, from 1 to 50 micron (±10-15%), as measured by ellipsometry.

Analyte Measurements

All measurements utilized wetted biosensors (i.e., sensors presoaked in deionized water and test buffer). The biosensor was washed with deionized water to a constant output value (that is, it maintained the same impedance value upon further washing). This established a baseline value for the sensor in absence of ligand. Test samples in buffer were then added. Output (changes in impedance, etc) was recorded as a function of time.

Figure 2:
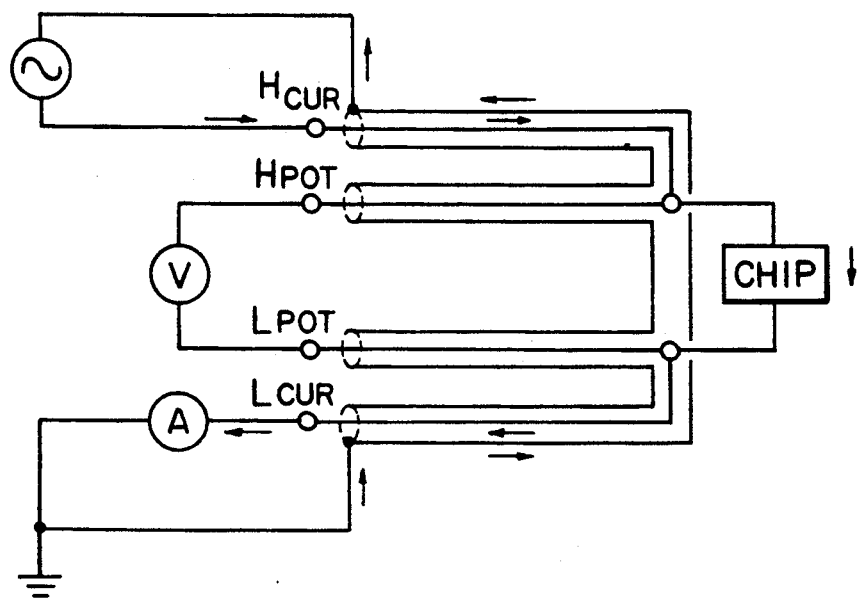
FIG. 2 is a schematic representation of a single chip test circuit.

Two approaches were used to evaluate the functionality of the two types (i.e., receptor and antibody-based) of biosensors. In the first approach, measurements were taken sequentially on control and test sensors ("chips") and compared. This approach can be done quickly for rapid evaluation of a sensor (FIGS. 1 and 3). However, background (i.e., non specific binding to the sensor) is not subtracted out automatically. A second configuration, as shown in FIGS. 2 and 4, which utilizes a sensor incorporating both a reference (control) and a test membrane ("double membrane chips") was also used. This allows for simultaneous challenge (i.e., challenge of both the control and the receptor-containing biosensor at the same time) and background is automatically subtracted out.

In the case in which sequential measurements were used, alternating current measurements were made on the sensors, and changes were recorded in impedance (measured in ohms), capacitance or phase angle. Samples in volumes of 5 to 200 microliters (ul) were analyzed; concentrations in such solutions were approximately 0.1 to 500 micrograms/ml (ug/ml).

Typically, a sample to be tested (i.e., one thought to contain an analyte of interest) was applied to a sensor which had been previously equilibrated with deionized water and readings of output impedance from the sensor were taken. Equilibration to constant readings occurred within 2 to 10 sec. Readings remained stable for at least the 5 minutes during which the output was routinely monitored. The sensor was then washed with deionized water to background equilibrium, sample was again added and readings were taken. In each case 2 to 5 cycles were carried out in this way.

Results showed that in the case of reversibly binding analytes of interest, (such as acetylcholine (ACh) for the AChR), analyte can be quickly washed out of the sensor and the sensor will then, reproducibly, re-react with the analyte. As shown in Table 4, in one series with ACh and an AChR sensor, repeated applications (after washing) on the same sensor with ACh solutions of the same concentration resulted in less than 3% variation among readings.

TABLE 4

Reproducibility of Test Data With Sequential Addition of Test Agent[a]

| Step[b] | KΩ | | |
|---|---|---|---|
|  | Test 1[c] | Test 2 | Test 3 |
| Background | 240.0 | 247.0 | 243.0 |
| Add Sample | 26.5 | 27.2 | 17.4 |
| Wash | 236.0 | 250.0 | 247.0 |
| Add Sample | 27.1 | 29.5 | 16.7 |
| Wash | 230.0 | 245.0 | 247.0 |

[a]Using an AChR sensor and ACh as the test agent.
[b]Each step reached equilibrium within 1 min.
[c]Test samples were 50 to 100 ul of solutions of ACh at concentrations: 1, 500 ug/ml; 2, 50 ug/ml; 3, 5 ug/ml.

The same was shown to be true of all other AChR sensors tested. Additionally, in the dose-response experiments described below, in which a single sensor was used in assessing device-to-device variability, results showed that a single sensor can be recycled at least 24 times with no apparent performance decrement.

Table 5 shows data from an assessment of dose-response to analytes of interest and a control substance (glucose) by the AChR sensor. Of particular interest in this table is the percentage change in resistance evident between control and AChR sensors. Glucose, which does not bind to the AChR, showed no change when applied to either sensor. ACh, the natural binding material for the AChR, showed a dose-dependent change in resistance which reached a change of over 100% at the highest concentration tests. Alpha-bungarotoxin (alpha- BTX) shows a similar dose response. Thus, the AChR sensor detects specific binding substances in a dose-dependent manner.

TABLE 5

Response of Control and AChR Sensors to Agent Challenge[a]

| Sensor[b] | Glucose | | | ACh | | | alphaBTX | | |
|---|---|---|---|---|---|---|---|---|---|
| | Conc.[c] | KΩ | % Change[d] | Conc. | KΩ | % Change | Conc. | KΩ | % Change |
| Control | 0.5 | 28 | — | — | — | — | — | — | — |
| | 5.0 | 33 | — | 5 | 23 | — | 5 | 42 | — |
| | 50.0 | 33 | — | 50 | 11 | — | 50 | 23 | — |
| | 500.0 | 58 | — | 500 | 4 | — | 500 | 13 | — |
| AChR | 0.5 | 29 | 3 | — | — | — | — | — | — |
| | 5.0 | 33 | 0 | 5 | 25 | 8 | 5 | 42 | 0 |
| | 50.0 | 35 | 6 | 50 | 17 | 55 | 50 | 34 | 48 |
| | 500.0 | 61 | 5 | 500 | 9 | 125 | 500 | 27 | 108 |

[a]Using an AChR sensor with ACh and alpha BTX as agents and glucose a control (non-binding) agent.
[b]Control sensor is the same formulation as AChR but with no AChR add
[c]From 50 to 100 uL of sample was applied per test. All tests in duplicate. Concentrations in ug/ml.
[d]With respect to control.

Preparation of Opiate Receptor

The OpR was prepared and assayed according to standard methods, which are described in the following references, the teachings of which are incorporated herein by reference: Zukin, R. S. and R. Maneckjee, *Methods in Enzymology*, 124:172-190 (1986); Simon, E. J., Methods in Receptor Research (Belcher, M., Ed.), pp. 497-510 (1976); Bruns, R. F. et al., *Analytical Biochemistry, chemistry*, 132:72-81 (1983); Howells, R. D., et al., *Journal of Pharmacology and Experimental Therapeutics*, 222:629-634 (1982); Ruegg, U. T. et al., *Proceedings of the National Academy of Sciences, USA*, 78:4635-4638 (1981); Simonds, E. F. et al., *Proceedings of the National Academy of Sciences, USA*, 77:4623-4627 (1980).

EXAMPLE 2

Opiate Receptor-Based Biosensor

This Example illustrates use of the opiate receptor (OpR) applied to an integrated electrode chip to yield an OpR-based biosensor.

The source of the OpR was rat brain. Brains were dissected immediately from rats after sacrificing and the cerebellums were removed and discarded. Approximately 20 g of the remaining brain tissue was homogenized in 200 ml of 0.32M sucrose using a tissue homogenizer. The homogenate was centrifuged at 1000 × g for 10 minutes at 4° C. and the supernatant was then recentrifuged at 15,000 × g for 15 minutes at 4° C. The resulting pellet (P2 fraction) represents a synaptosomal OpR fraction.

The P2 fraction was purified further by suspending it in 200 ml of 0.32M sucrose and treating aliquots of this suspension by the following method. Approximately 40 ml of the P2 suspension were diluted by the addition of 40 ml of 0.01M Tris-HCl buffer, pH 7.5, containing 20% (wt/vol) glycerol, 0.01 mM phenylmethylsufonyl fluoride, 10 mM MgSO4, 1 mM EDTA and 5 mM dithiothretol (Buffer #1). CHAPS detergent solution (1M 3[(3-chloramidopropyl)-dimethylammoniol] 1-propane sulfonate in 0.01M Tris-HCl buffer, pH 7.5) was added to the diluted P2 suspension to yield a final CHAPS concentration of 10 mM. The solution was homogenized and incubated for 15 to 20 minutes on ice. It was then centrifuged at 105,000 × g for 60 minutes at 4° C. The resulting supernatant contains the partially purified OpR.

The partially purified OpR can be further purified by one or both of the following methods. In the first, approximately 40 ml of the crude OpR solution was made to pH 5.6 by addition of 1M potassium acetate-acetic acid buffer, pH 5.6 (Buffer #2). Solid polyethylene glycol (PEG) was then added to the solution to a final concentration of 17% wt/vol). The solution was incubated at 4° C. for 15 to 20 minutes and then centrifuged at 20,000 × g for 20 minutes at 4° C. The resulting pellet was suspended in 10 ml of Buffer #1 containing 1 mM CHAPS (Buffer #3). This is the PEG-purified OpR. In the second purification method, approximately 3 to 5 ml (5 to 15 mg of protein) of either the crude OpR solution or the PEG-purified OpR solution was applied to a column (1 cm I.D. × 40-50 cm long) of Sepharose CL-6B, packed and pre-equilibrated with Buffer #3. The column was eluted with Buffer #2 and monitored at 180 nm to detect elution of protein. The OpR elutes from the column at approximately 40 to 50 ml of eluate. This is the GPC-purified OpR.

Assay of OpR

The OpR was assayed at the various purification levels using the binding of receptor-specific radioactive ligands: [$^3$H]etorphin [$^3$H]naloxone. The binding assays were carried out in the presence and absence of levorphanol, which binds non-specifically to the OpR. Specific binding to the OpR is defined as total binding of etorphine or naloxone with no levorphanol present minus opiate binding to the receptor in the presence of levorphanol. Typically, assay mixtures contained 1 to 10 nM etorphine or naloxone and 0.5 to 1 uM levorphanol together with the receptor preparation to be assayed. The final volume of the assay mixtures was made up to 0.5 or 1.5 ml with 10 mM Tris-HCl buffer, pH 7.4 containing 1 mM CHAPS. The procedure followed for the assays and separation of free and bound ligand on glass-fiber filters was according to Zukin, R. S. and R. Maneckjee, *Methods in Enzymoloqy*, 124:172-190 (1986).

The OpR was successfully isolated from rat brain tissue using the methods described above. Table 6 reports the binding of etorphine and naloxone to the various OpR preparations. The amounts bound are in agreement with published values for the binding of these ligands to the OpR from animal brain.

TABLE 6

Binding Activity of the OpR Purification Fractions[a]

| Fraction[b] | Ligand | pmol Bound/mg Protein[c] |
|---|---|---|
| Crude homogenate | Etorphine | 0.007 |
| P2 Fraction | Etorphine | 0.013 |
| | Naloxone | 0.020 |
| PEG-Purified | Etorphine | 0.028 |

TABLE 6-continued

| Binding Activity of the OpR Purification Fractions[a] | | |
|---|---|---|
| Fraction[b] | Ligand | pmol Bound/mg Protein[c] |
| GPC-Purified | Etorphine | 0.028 |

[a]All assays were carried out in a total volume of 0.5 ml with ligand concentrations of 10 nM.
[b]See the text for descriptions of the purification fractions.
[c]Corrected for non-specific binding in the presence of 400 nm levorphanol.

Immobilization of the OpR

The basic membrane preparation for the OpR was as described in Example 1 for the acetylcholine receptor preparation Bovine serum albumin (BSA, 99% globulin free, Sigma Chemical Co., St. Louis, Mo.) was used as the base membrane material. Typically, 150 mg of BSA, stabilizer (for example, 15 mg phosphatidyl choline), and mg CHAPS were solubilized in 2.5 ml of 10 mM Tris-CHI buffer, pH 7.5 for control (non-receptor containing) membranes. For OpR containing membranes, the BSA, stabilizer and CHAPS were solubilized in 2.5 ml of the OpR preparation to be used. Gluraraldehyde (1 to 5% by weight) was then added to effect polymerization. Approximately 2 to 10 mg OpR protein was present in such membranes. The membranes were cast either on glass plates for stability studies, or onto interdigitated electrode transducers.

In another example, the OpR was immobilized in gelatin membranes. In this case, 50 to 100 mg of gelatin (from bovine skin, approximately 225 Bloom, Sigma Chemical Co.) with or without stabilizer were solubilized in 2.5 ml of OpR preparation (containing 2 to 10 mg of OpR protein). Gluraraldehyde (from 2 to 10% by weight) was then added to effect polymerization.

OpR Interdigitated Transducer Chips

The OpR was applied to quartz chips containing interdigitated gold electrodes as presented in FIG. 1 and described above. In this case, only BSA membranes were applied to the chips. It appears that gelatin membranes could also be applied to the chips since it was found that the OpR could be successfully immobilized into such membranes. For example, in comparison to a control gelatin membrane containing no OpR, gelatin membranes containing 2.1 mg of P2 OpR preparation protein bound 35% more ligand than the control membrane when challenged with 1.67 nM etorphine (approximately 0.7 parts-per-billion). This increased binding represents specific binding to the immobilized receptor.

Table 7 presents data confirming the response of OpR-containing transducers to challenge opiates. In these studies, the chips were challenged with low concentrations of ligands (parts-per-billion range) and thus large differences in resistance changes between the control and test chips were not seen. It was observed that a significant difference of 17% was seen between the control and test chips when challenged with naloxone (which binds to both the specific binding site and secondary sites on the opiate receptor), and a 10% difference was seen when the chips were challenged with levorphanol (which binds to secondary sites on the opiate receptor).

TABLE 7

| Response of the OpR Biosensor to Opiates[a] | | |
|---|---|---|
| Ligand (Concentration) | $\Delta K\Omega$[b] | $\Delta\%$[c] |
| Naloxone (648 ppb)[d] | −147 | 17% |

TABLE 7-continued

| Response of the OpR Biosensor to Opiates[a] | | |
|---|---|---|
| Ligand (Concentration) | $\Delta K\Omega$[b] | $\Delta\%$[c] |
| Levorphanol (514 ppb) | −160 | 10% |

[a]The sensor chips were coated with a BSA membrane containing (wt/vol) 6% BSA, 0.6% phosphatidyl choline, 2% CHAPS and from 4 to 5 mg of OpR protein (P2 fraction). Control chips did not contain the OpR.. Polymerization of the membrane was effected by addition of glutaraldehyde to a final concentration of 1% (wt/vol). Each test chip contained from 0.09 to 0.12 mg of OpR protein.
[b]The change in resistance across the biosensor circuit when challenged with agent. Values are the mean of from 6 to 10 different challenges using from 3 to 5 different chips. The standard deviation from the mean for any trial or chip was never more that ±9%. Control chips containing no OpR typically showed resistance changes of approximately - 180 kΩ.
[c]The percent difference between the resistance changes of the test and control chips when challenged with the ligand.
[d]For this concentration, 50 ul of a 2 uM solution of ligand was applied to the chip.

The results confirm that an OpR-based biosensor can be made. The successful immobilization and integration of the OpR onto an electronic transducer provides a second, specific example for applying this technology to receptor molecules. The specific OpR-based biosensor described will have application to detection, quantification and diagnosis of opiates, narcotics and drugs binding to and affecting the opiate receptor.

EXAMPLE 3

Immunoglobulin-Based Biosensors

This Example illustrates the use of immobilized human immunoglobulin G as a receptor in a biosensor of the present invention. Table 8 shows results of an assessment of biosensors in which the receptor is immobilized human IgG. Challenge of the sensors with antibody to IgG (alphaIgG) resulted in significant resistance changes. This demonstrates that the technology is also applicable to antibody-based biosensors.

TABLE 8

| Response of Control and IgG Sensors to Challenge by alphaIgG[a] | | |
|---|---|---|
| Sensor[b] | Response (KΩ) | % Change[c] |
| Control | | |
| #1 | 136 | — |
| #2 | 86 | — |
| IgG | | |
| #1 | 280 | +105% |
| #2 | 248 | +188% |

[a]AC impedance measurements at 120 Hz using deionized water as the electrolyte. Challenge was with antibody to IgG (alpha IgG) using a 10 uL test solution volume containing approximately 500–700 ug alpha IgG.
[b]Control sensor differs only in that it does not contain IgG. The IgG sensor membrane contained 25% by weight human IgG.
[c]With respect to control.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. An opiate receptor-containing biosensor for the determination of an opiate in a sample comprising:
   a) a polymeric film formed by chemical copolymerization of a solution comprising:
      1) a base component which is a protein,
      2) an opiate receptor; and
      3) at least one stabilizer selected from the group consisting of lipids, detergents and antioxidants;

b) a first sensor comprising a first conductor and a second conductor which are in contact with said film; and c) a current source in conductive contact with the first and second conductors for measuring an electrical characteristic of the polymeric film.

2. An opiate receptor-containing biosensor of claim 1 wherein the protein is selected from the group consisting of serum albumin, gelatin and collagen.

3. An opiate receptor-containing biosensor of claim 1 wherein the lipid is selected from the group consisting of: phosphatidyl choline and cholesteryl palmitate, the detergent is selected from the group consisting of octylphenoxy polyethoxethanol, sodium cholate, cetyltrimethyl-ammonium bromide, polyoxyethylene, sorbitan monooleate, N-decyl-N-dimethyl-3-ammonio-1-propane sulfonate and N-octyl-N-dimethyl-3-ammonio-1-propane sulfonate, and the antioxidant is selected from the group consisting of alphatocopherol and butylated hydroxyanisole.

4. A double chip, opiate receptor-containing biosensor for the determination of an opiate in a sample, comprising a first polymeric film comprising a protein, a stabilizer and an opiate receptor, the first polymeric film being in contact with a first electrical sensor for measuring an electrical characteristic of the first polymeric film and further comprising:

a) a second nonreceptor containing polymeric film, the second polymeric film being in contact with a second electrical sensor for measuring an electrical characteristic of the second polymeric film;

b) a potential barrier interposed between the second nonreceptor containing film and the first polymeric film, such that the barrier hinders current flow between said second nonreceptor containing film and the first polymeric film;

c) a current source; and d) a circuit contacting the current source and the first and the second electrical sensors for measuring the absolute and the differential changes in the electrical characteristics of the first and second films.

5. An opiate receptor-containing biosensor of claim 1 wherein the protein is selected from the group consisting of serum albumin, gelatin and collagen.

6. An opiate receptor-containing biosensor of claim 4 wherein the lipid is selected from the group consisting of: phosphatidyl choline and cholesteryl palmitate, the detergent is selected from the group consisting of octylphenoxy polyethoxethanol, sodium cholate, cetyltrimethyl-ammonium bromide, polyoxyethylene, sorbitan monooleate, N-decyl-N-dimethyl-3-ammonio-1-propane sulfonate and N-octyl-N-dimethyl-3-ammonio-1-propane sulfonate, and the antioxidant is selected from the group consisting of alphatocopherol and butylated hydroxyanisole.

7. A method of immobilizing and stabilizing an opiate receptor in a polymeric film on a transducer, comprising:

a. forming a mixture by combining an opiate receptor, a base component which is a protein, a polymerizing agent and at least one stabilizer selected from the group consisting of lipids, detergents and antioxidants, under conditions appropriate for polymerization to occur; and b. forming a film by polymerization of the mixture of a) on the transducer.

8. A method of claim 7 wherein the base component is selected from the group consisting of bovine serum albumin, human serum albumin, gelatin and collagen; the polymerizing agent is glutaraldehyde; the lipid is selected from the group consisting of: phosphatidyl choline and cholesteryl palmitate, the detergent is selected from the group consisting of octylphenoxy polyethoxethanol, sodium cholate, cetyltrimethylammonium bromide, polyoxyethylene, sorbitan monooleate, N-decyl-N-dimethyl-3-ammonio-1-propane sulfonate and N-octyl-N-dimethyl-3-ammonio-1-propane sulfonate, and the antioxidant is selected from the group consisting of alphatocopherol and butylated hydroyanisole.

9. A method for determining the presence of an opiate in a sample comprising:

a) contacting the sample with a biosensor comprising:
1) a polymeric film formed by chemical copolymerization of a solution comprising:
a) a base component which is a protein;
b) an opiate receptor capable of binding the analyte; and
c) at least one stabilizer selected from the group consisting of lipids, detergents and antioxidants; and
2) a sensor comprising a first conductor and a second conductor which are in contact with the polymeric protein film; and b) determining a change in the electrical characteristic of the polymeric protein film, whereby a change is indicative of the presence of analyte in the sample.

* * * * *

UNITED STATES PATENT AND TRADEMARK OFFICE
CERTIFICATE OF CORRECTION

PATENT NO. : 5,192,507

DATED : March 9, 1993

INVENTOR(S) : Richard F. Taylor, Ingrid G. Marenchic, Edward J. Cook

It is certified that error appears in the above-identified patent and that said Letters Patent is hereby corrected as shown below:

Column 17, claim 5, line 42, delete "1" and insert --4--

Signed and Sealed this

Eighteenth Day of January, 1994

Attest:

BRUCE LEHMAN

*Attesting Officer*  *Commissioner of Patents and Trademarks*